United States Patent [19]

Brunelle et al.

[11] Patent Number: 4,513,141

[45] Date of Patent: Apr. 23, 1985

[54] METHOD FOR MAKING AROMATIC ETHERS USING DIORGANOAMINO PYRIDINUM SALT CATALYST

[75] Inventors: Daniel J. Brunelle, Scotia, N.Y.; Daniel A. Singleton, Minneapolis, Minn.

[73] Assignee: General Electric Company, Schenectady, N.Y.

[21] Appl. No.: 489,689

[22] Filed: Apr. 28, 1983

[51] Int. Cl.$^3$ .................. C07B 29/00; C07D 207/444; C07C 41/01
[52] U.S. Cl. ..................................... 548/476; 548/480; 548/455; 546/304; 260/465 F; 568/31; 568/37; 568/43; 568/45; 568/315; 568/584
[58] Field of Search ................ 546/304; 548/476, 455, 548/480; 260/465 F; 568/31, 37, 43, 45, 315, 584

[56] References Cited

U.S. PATENT DOCUMENTS

| | | | |
|---|---|---|---|
| 3,852,242 | 12/1974 | White | 260/47 CZ |
| 4,140,853 | 2/1979 | Vorbrueggen | 544/60 |
| 4,158,093 | 6/1979 | Bailey et al. | 542/455 |
| 4,202,993 | 5/1980 | Takekoshi | 568/723 |
| 4,257,953 | 3/1981 | Williams et al. | 260/326 R |
| 4,273,712 | 6/1981 | Williams | 260/326 N |

FOREIGN PATENT DOCUMENTS

1539183  1/1979  United Kingdom .

OTHER PUBLICATIONS

Merck Index, 9th Edition entry #1987 (1976).
4-Dialkylaminopyridines as Highly Active Acylation Catalysts, Hofle et al., Angew. Chem. Int. Ed. Engl. 17, 569-583 (1978).
Phosphoramides; VIII[1]. Phosphorus Pentoxide/Amine Mixtures as Reagents in a Facile Synthesis of Dialkylaminopyridines, Pedersen et al., Synthesis, 844, (1978).
Synthesis and Catalytic Activity of Polymer-Bound 4-(N-Benzyl-N-Methylamino)Pyridine, Tomoi et al., Makromol, Chem., Rapid Commun. 3, 537-542 (1982).
Phase Transfer Catalysis, Starks et al., Academic Press, New York (1978).
Phase Transfer Catalysis, Dehmlow et al., Verlag Chemie, Stuttgart, Germany (1980).
Phase Transfer Catalysis in Organic Synthesis, Weber et al., Springer-Verlag, New York (1977).

*Primary Examiner*—Henry R. Jiles
*Assistant Examiner*—Dale A. Bjorkman
*Attorney, Agent, or Firm*—William A. Teoli; James C. Davis, Jr.; James Magee, Jr.

[57] ABSTRACT

A method is provided for making aromatic ethers by effecting the displacement of reactive radicals on an activated aromatic nucleus such as a phthalimide with a mono or bisalkali metal phenoxide in the presence of an organic solvent and a dialkylamino branched alkyl substituted pyridinium salt as a phase transfer catalyst. Improved yields of bis(aromatic ethers) are achieved without the production of undesirable by-products, such as alkylated phenols.

18 Claims, No Drawings

METHOD FOR MAKING AROMATIC ETHERS USING DIORGANOAMINO PYRIDINUM SALT CATALYST

CROSS REFERENCE TO RELATED APPLICATIONS

Reference is made to the copending application of Daniel J. Brunelle, RD-14979, for Phase Transfer Catalysts, filed concurrently herewith and assigned to the same assignee as the present invention.

BACKGROUND OF THE INVENTION

As shown by Williams, U.S. Pat. No. 4,273,712, and Williams U.S. Pat. No. 4,257,953, assigned to the same assignee as the present invention, methods are provided for making aromatic bis(etherimide)s of the formula,

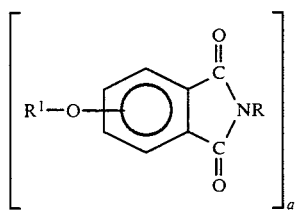

where R is a monovalent radical selected from hydrogen, a $C_{(1-8)}$ alkyl radical and $C_{(6-13)}$ aryl radical, $R^1$ is a $C_{(6-30)}$ aromatic organic radical, and a is an integer equal to 1 or 2, and when a is 1, $R^1$ is monovalent and when a is 2, $R^1$ is divalent. Reaction is effected between a substituted phthalimide of the formula,

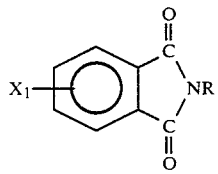

and an alkali metal phenoxide of the formula,

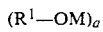

$$(R^1-OM)_a \qquad (3)$$

in the presence of a nonpolar organic solvent and a phase transfer catalyst, where R, $R^1$ and a are as previously defined, $X_1$ is a radical selected from nitro and halo, and M is an alkali metal ion.

The phase transfer catalyst utilized by Williams and Williams et al are tetraorgano ammonium or phosphonium salts, for example, tetraalkylammonium salts, which allow for the production of aromatic etherimides in the absence of a dipolar aprotic solvent. Although valuable results are obtained in accordance with the practice of the Williams, or Williams et al methods, the quaternary ammonium or phosphonium salts are often found to be unstable. The instability of these tetraalkyl salt phase transfer catalyst can result in undesirable phenol alkylation and recycling problems.

The present invention is based on the discovery that aromatic ethers including the etherimides of formula (1) can be obtained without phenol alkylation by utilizing as a phase transfer catalyst in the condensation reaction between a nuclear activated aromatic compound substituted with a leaving group selected from nitro or halo such as the substituted phthalimide of formula (2), and the alkali metal phenoxide of formula (3), an effective amount of a diorganoaminopyridinium salt of the formula,

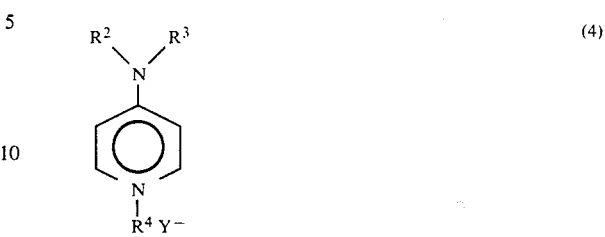

where $R^2$ and $R^3$ are monovalent or divalent organo radicals selected from $C_{(1-13)}$ hydrocarbon radicals and $C_{(1-13)}$ substituted hydrocarbon radicals and $C_{(1-8)}$ divalent alkylene radicals which can be part of a cyclic structure forming a $C_{(4-12)}$ ring, $R^4$ is selected from $C_{(4-18)}$ linear or branched alkyl radicals and Y is a counter ion. These diorganoaminopyridinium salts, unlike aminopyridinium salts have also been found to be highly stable as compared to the tetraorganoammonium, or phosphonium salts of Williams, or Williams et al referenced above.

As utilized hereinafter, the term "phase transfer catalyst stability" means the half-life of the catalyst as determined by heating an equal molar amount of phase transfer catalyst and the disodium salt of bisphenol-A in toluene under sealed conditions for a particular period of time which can vary between one-half hour or less to 16 hours or more. Assuming a pseudo-first order for decomposition of the phase transfer catalyst, the amount of catalyst remaining after a certain heating period as determined by NMR analysis can be extrapolated or interpolated to determine the midpoint of the linear plot. This procedure is shown by J. March, "Advanced Organic Chemistry", 2nd Ed., pp. 199–202. This procedure will provide a plot of ln[catalyst] vs. time, and should yield a linear plot.

STATEMENT OF THE INVENTION

There is provided by the present invention a method for making an aromatic ether which comprises, (A) heating a nuclear activated aromatic compound substituted with a leaving group selected from nitro or halo and an alkali metal phenoxide salt in the presence of organic solvent and an effective amount of a phase transfer catalyst of formula (4), (B) agitating the resulting mixture with a precipitating or extractive organic solvent for the resulting aromatic ether, or allowing the mixture to cool and (C) recovering the aromatic ether from the mixture of (B).

Radicals included by R, are for example, phenyl, tolyl, xylyl, naphthyl, chlorophenyl, bromonaphthyl, etc., and $C_{(1-8)}$ alkyl radicals such as methyl, ethyl, propyl, etc. Radicals included by $R^1$ are the aforementioned aromatic radicals, such as phenylene, tolylene, naphthylene, and $R^1$ more particularly includes

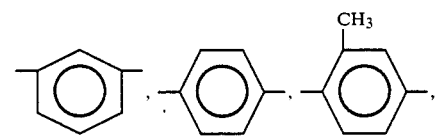

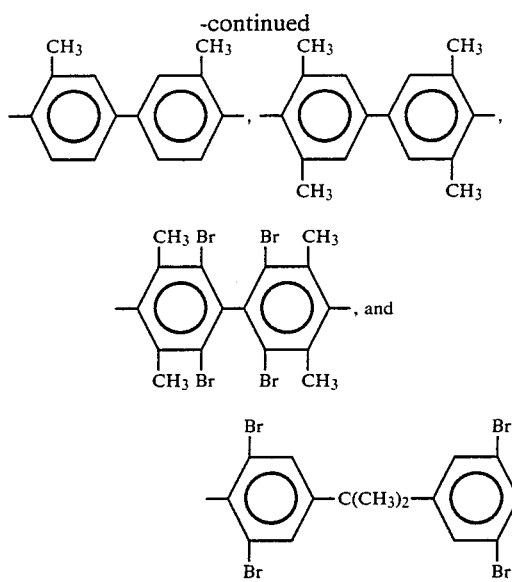

and divalent organic radicals of the general formula,

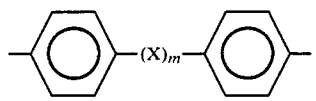

where X is a member selected from the class consisting of divalent radicals of the formula,

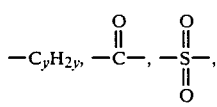

—O— and —S—, where m is 0 or 1, y is a whole number from 1 to 5.

M is more particularly sodium, potassium, lithium, rubidium, etc.; counter ions included by formula (4) are, for example, fluoride, chloride, bromide, methane sulfonate, nitrite, acetate, etc.

There are included within the nuclear activated aromatic compounds substituted with a leaving group selected from nitro or halo which can be used to make aromatic ethers in accordance with the practice of the method of the present invention, aromatic compounds such as
4-chloronitrobenzene;
2-chloronitrobenzene;
4-fluoronitrobenzene;
2-fluoronitrobenzene;
p-dinitrobenzene;
o-dinitrobenzene;
4,4'-dichlorbenzobenzophenone;
bis(p-chlorophenyl)sulfone;
p-chlorophenyl phenyl sulfone;
4-fluorobenzonitrile;
4-chlorobenzonitrile, etc.

Some of the substituted phthalimides which are included within formula (2) are for example,
4-nitro-N-phenylphthalimide;
3-nitro-N-phenylphthalimide;
4-nitro-N-methylphthalimide;
3-nitro-N-methylphthalimide;
4-fluoro-N-methylphthalimide;
4-fluoro-N-methylphthalimide;
4-chloro-N-methylphthalimide;
3-chloro-N-methylphthalimide, etc.

These substituted phthalimides can be made by standard procedures, such as effecting reaction between substantially equal moles of the corresponding phthalic anhydride and an organic amine in the presence of refluxing acetic acid. Included by the organic amines which can be used, are, for example, aniline, toluidene, etc., methylamine, ethylamine, etc.

Among the alkylaminopyridines of formula (4) which can be used as phase transfer catalysts in the practice of the method of the present invention are the corresponding chloride, bromide, methane sulfonate and nitrite salts of
N-(2-ethylhexyl)-4-dimethylaminopyridine;
N-(2-ethylhexyl)-4-(4-methylpiperidinyl)pyridine;
N-(2-ethylhexyl)-4-dibutylaminopyridine;
N-(2-ethylhexyl)-4-dihexylaminopyridine;
N-neopentyl-4-(4-methylpiperidinyl)pyridine;
N-neopentyl-4-dibutylaminopyridine;
N-neopentyl-4-dihexylaminopyridine;
N-octyl-4-dimethylaminopyridine;
N-butyl-4-dimethylaminopyridine;
N-dodecyl-4-dimethylaminopyridine.

Experience has shown, the most stable diorganoaminopyridinium salts of formula (4) are compounds having the formula,

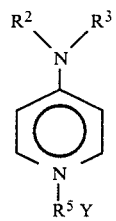

where $R^2$, $R^3$ and Y are as previously defined and $R^5$ is a $C_{(5-12)}$ neopentyl radical, for example,
N-neopentyl-4-(N',N'-dibutylamino)pyridinium chloride,
N-neopentyl-4-(4-methylpiperidino)pyridinium chloride, etc.

Precursors of some of the diorganoaminopyridinium salts of formula (4) can be made by reacting 4-hydroxypyridine with phosphorous pentoxide and a diorganoamine at 200° C. to 300° C., for example, 250° C. as shown by the following equation:

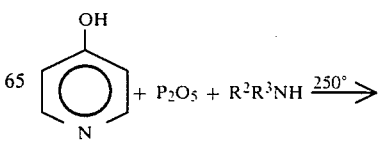

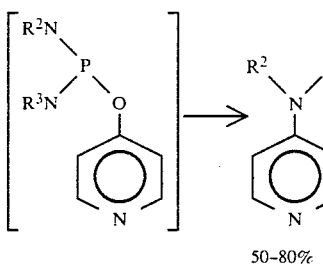

50-80% where $R^2$ and $R^3$ are as previously defined.

The alkylation of the above diorganoaminopyridines can be achieved in a straight forward manner utilizing such reagents as methyliodide, N-butylbromide, or N-hexylbromide at ambient temperatures in an inert organic solvent, for example, chloroform or toluene. Reaction with branched alkyl compounds such as isobutylbromide, tosylate or mesylate is facilitated by using higher temperatures such as refluxing toluene. Higher temperatures are required with neopentyltosylate or mesylate, for example 100° to 150° C.

The alkali metal salts of formula (3) can be made by various procedures, including the flash evaporation of bisphenoxide alkali metal salt hydrate or an aqueous slurry thereof, as shown by U.S. Pat. No. 4,202,993, Takekoshi, or by azeotroping water from an aqueous mixture of bisphenoxide alkali metal salt and toluene as shown by Williams et al U.S. Pat. No. 4,257,953. Additional procedures are shown in White U.S. Pat. No. 3,852,242, assigned to the same assignee as the present invention.

Some of the alkali metal salts of the abovedescribed alkali phenoxides of formula (3) are sodium and potassium salt phenols, such as phenol, cresol, naphthol, etc.; dihydric phenols, for example, 2,2-bis(2-hydroxyphenyl)propane;
2,4'-dihydroxydiphenylmethane;
bis(2-hydroxyphenyl)methane;
2,2-bis(4-hydroxyphenyl)propane, hereinafter identified as "bisphenol-A" or "BPA";
1,1-bis(4-hydroxyphenyl)ethane;
1,1-bis(4-hydroxyphenyl)propane;
2,2-bis(4-hydroxyphenyl)pentane;
3,3-bis(4-hydroxyphenyl)pentane;
4,4'-dihydroxybiphenyl;
4,4'-dihydroxy-3,3,5,5'-tetramethylbiphenyl;
2,4'-dihydroxybenzophenone;
4,4'-dihydroxydiphenylsulfone;
2,4'-dihydroxydiphenylsulfone;
4,4'-dihydroxydiphenylsulfoxide;
4,4'-dihydroxydiphenylsulfide;
hydroquinone;
resorcinol;
3,4'-dihydroxydiphenylmethane;
4,4'-dihydroxybenzophenone; and
4,4'-dihydroxydiphenylether.

In the practice of the invention, reaction is effected between the nuclear substituted activated aromatic compound and the phenoxide salt which hereinafter will signify either the mono- or dihydric phenol salt in the presence of a nonpolar solvent and an effective amount of a phase transfer catalyst, followed by the recovery of the resulting "aromatic ether" which hereinafter can signify either aromatic ether phthalimide, aromatic bis(ether phthalimide), or other aromatic ethers. It is preferred to effect reaction under substantially anhydrous conditions, although small amounts of moisture can be tolerated.

Temperatures at which reaction between the phenoxide salt and the nuclear substituted activated aromatic compound can be effected are in the range of about between 25° C. to 200° C., and preferably a temperature between 100°–150° C. Any nonpolar organic solvent which does not react with the reactants during the formation of the aromatic ether can be used in the reaction. Some of the nonpolar organic solvents are, for example, toluene benzene, chlorobenzene, dichlorobenzene, xylene, tetrahydrofuran, acetonitrile, octane, etc.

Experience has shown that the reaction can best be run using a solids concentration in the range of between about 5% to 150% by weight of solids, based on the total volume of non-polar solvent used, and preferably from between about 85–95% by weight. Preferably, equivalent amounts of the phenoxide salt and an activated aromatic compound can be used, while higher or lower amounts of either reactant will not substantially interfere with the formation of the desired aromatic ether. In preparing the aromatic ether there is preferably used about 2 moles of the nuclear substituted activated aromatic compound, per mole of the bisphenoxide salt. The phase transfer catalyst as previously defined, can be utilized at from 0.001 equivalent to 2 equivalents of catalyst, per equivalent of alkali bisphenoxide and preferably from 0.005 to 0.02 equivalent.

The aromatic ether can be recovered from the reaction mixture by a variety of procedures. One procedure, for example, can be by allowing the reaction mixture to cool, followed by recovery of the aromatic ether by filtration. It is preferred, however, because of the partial solubility of the aromatic ether in various nonpolar organic solvents, to precipitate the aromatic ether by use of a precipitating solvent, for example, methanol, followed again by a standard recovery technique, such as filtration. Alternatively, aromatic ether can be extracted from the reaction mixture with a better solvent such as methylene chloride, chloroform, etc., washed with water to effect removal of the inorganic salts, and recovered by the removal of the organic solvent under reduced pressure.

Experience has shown that the phase transfer catalysts and by-products of the reaction can be recycled directly for further use in the production of aromatic ether phthalimide in accordance with the practice of the invention. For example, in the situation where the reaction mixture is allowed to cool to room temperature to effect the separation of aromatic ether, the filtrate can be reused as a source of the phase transfer catalyst and the nonpolar organic solvent. In instances where a precipitating solvent is employed to effect the separation of aromatic ether, the filtrate can be evaporated to dryness to recover the phase transfer catalyst which can be recycled.

In order that those skilled in the art will be better able to practice the invention, the following examples are given by way of illustration and not by way of limitation. All parts are by weight.

EXAMPLE 1

There are prepared 4-dibutylaminopyridine by adding 0.1 mole of 4-hydroxypyridine and 15 grams of phosphorous pentoxide in the presence of 0.2 mole of dibutylamine at 250° C. for 16 hours. The dimethylaminopyridine was obtained from the Aldrich Chemical Company of Milwaukee, Wis. and the 4-pyrrolidinopyridine was obtained from the Reilley Tar and Chemical Company, Indianapolis, Ind.

Neopentylmethanesulfonate (10 mmoles) and 4-N'-N'-dibutylaminopyridine (10 mmoles) were heated together at 130° C. for 72 hours. The reaction mixture was then poured into 50 ml of saturated aqueous sodium bromide. The mixture was made basic with 50% sodium hydroxide, washed twice with 50 ml pentane and then acidified with concentrated HBr. The aqueous phase was then extracted three times with 50 ml of methylene chloride. The extracts were combined and rotoevaporated. The resulting solid was dissolved in a minimum amount of 2-propanol and crystallized by slow addition of ethylether. The resulting salt was isolated by vacuum filtration, rinsed with ethylether and dried under vacuum at room temperature. There was obtained an 80% yield of product. Based on method of preparation, there was obtained N-neopentyl-4-N'-N'-dibutylaminopyridinium bromide (NPDBAPB). Its identity was further confirmed by NMR (CDCl$_3$): 8.58 ppm (d, J=8 Hz, 2H, 2,6-pyridyl); 6.95 (d, J=8 Hz, 2H, 3,5-pyridyl); 4.25 (s, 2H, neopentyl methylene); 3.50 (t, J=8 Hz, 4H, methylenes of butyl chain adj. to N); 2.5–1.9 (m, 8H, methylenes of butyl chains); 0.9–1.2 (m, 15H, methyl groups).

The above procedure was repeated utilizing 4-dihexylaminopyridine resulting in the production of N-neopentyl-4-N',N'-dihexylaminopyridinium bromide (NPDHAPB) which was recovered at a 70% yield. Its identity was further confirmed by NMR (CDCl$_3$): 8.58 ppm (d, J=8 Hz, 2H, 2,6-pyridyl); 6.88 (d, J=8 Hz, 2H, 3,5-pyridyl); 4.24 (s, 2H, neopentyl methylene); 3.48 (t, J=8 Hz, 4H, CH$_2$ adj. to N); 1.2–1.9 (m, 16H, methylenes of hexyl chains); 0.9–1.2 (m, 15H, methyl groups).

A study was conducted to compare the stability of the above dialkylpyridinium salts with tetrabutylammonium bromide in a solution of sodium cresoxide in dimethylsulfoxide and the disodium salt of bisphenol-A in toluene. The degree of catalyst decomposition in dimethylsulfoxide was determined by NMR analysis. The toluene mixtures were cooled, quenched with water, and extracted into methylene chloride. The amount of residual catalyst was also determined by NMR analysis using tetrachlorobenzene as an internal standard.

All of the mixtures studied were evaluated in a vial. The following results were obtained, where the temperature, time of heating and percent decomposition are shown:

TABLE I

| | Temp | Time | % Decomposition |
|---|---|---|---|
| (C$_4$H$_9$)$_4$NBr | 110 | 2 hr | 90% |
| (C$_4$H$_9$)$_4$NBr | 150 | 30 min | 100% |
| NPDBAPB | 150 | 30 min | 15% |
| (C$_4$H$_9$)$_4$NBr | 110 | 30 min[a] | 92% |
| NPDBAPB | 110 | 16 hr[a] | 64% |

[a]Reaction in toluene with BPA disodium salt.

The above result show that the dialkylpyridinium salts utilized in the practice of the present invention have a higher stability in organic solvents containing alkali metal phenoxides or disphenoxides than the corresponding tetra-alkyl ammonium salts.

EXAMPLE 2

A mixture of 0.10 mole of parachloronitrobenzene were heated together with 1.0 mmole sodium phenoxide or cresoxide in 10 ml of toluene along with 5.15 milligram per ml of n—C$_{17}$H$_{35}$ as an internal standard. The various mixtures were combined with effective amounts of phase transfer catalysts and stirred and heated at the same time and temperature. Analysis of the resulting reaction products were obtained by VPC analysis on OV-17 column. The yields of para-nitrophenylphenylether and the reactions conditions were shown in Table II below, where Bu$_4$NBr is tetrabutylammonium bromide:

TABLE II

| Catalyst | (Mole %) | Time | Yield |
|---|---|---|---|
| Bu$_4$NBr | (5) | .25 | 0 |
| Bu$_4$NBr | (5) | 1.0 | .5 |
| Bu$_4$NBr | (5) | 4.0 | 1.1 |
| Bu$_4$NBr | (20) | .25 | 3.1 |
| Bu$_4$NBr | (20) | 1.0 | 12.7 |
| Bu$_4$NBr | (20) | 4.0 | 18.2 |
| Bu$_4$NBr | (20) | 12 | 18.9 |
| NPDBAPC[a] | (5) | .25 | .9 |
| NPDBAPC | (5) | 1.0 | 5.0 |
| NPDBAPC | (5) | 4.0 | 12.6 |
| NPDBAPC | (20) | .25 | 4.1 |
| NPDBAPC | (20) | 1.0 | 16.7 |
| NPDBAPC | (20) | 4.0 | 53.5 |
| NPDBAPC | (20) | 12 | 84 |
| NPDHAPB[b] | (20) | .25 | 3.6 |
| NPDHAPB | (20) | 1.0 | 20.1 |
| NPDHAPB | (20) | 4.0 | 41.6 |
| NPPPB[c] | (20) | 25 | 0 |
| NPPPB | (20) | 1.0 | 1.8 |
| NPPPB | (20) | 4.0 | 11.9 |
| NPDMAPB[d] | (20) | .25 | 0.6 |
| NPDMAPB | (20) | 1.0 | 2.2 |
| NPDMAPB | (20) | 4.0 | 21.7 |

[a]Neopentyldibutylaminopyridinium chloride
[b]Neopentyldihexylaminopyridinium bromide
[c]Neopentylpyrroidinopyridinium bromide
[d]Neopentyldimethylaminopyridinium bromide The above results show that dialkylaminopyridinium salts are superior to tetra-alkylammonium halides as phase transfer catalysts in condensation reaction between alkali metal phenoxides with halonitro aromatic hydrocarbons in non-polar organic solvents. Higher yields of product were obtained in certain cases with the tetraalkylammonium salts using a concentration four times greater than the 5 mol percent of the dialkylaminopyridinium salt.

EXAMPLE 3

A mixture of 2.01 moles of 4-nitro-N-methylphthalimide, an effective amount of a phase transfer catalyst shown below in Table III and 102 milligrams of fluorenone (internal standard) was dried in an air oven at 104° C. for 1 hour. The resulting mixture was allowed to cool under sealed conditions to ambient temperatures in a drybox. There was then added 1.0 mmole of the disodium salt of bisphenol-A to the resulting mixture and the resulting mixture was then sealed and removed from the drybox. Toluene which had been distilled from sodium was added to the resulting mixture under a stream of nitrogen and the resulting mixture was then heated under sealed conditions from 1–2 hours. A crude reaction product was allowed to cool and diluted with chloroform. The solution was analyzed by high pressure liquid chromatography on a Dupont CN column eluting with THF/isooctane. The following results were obtained:

TABLE III

| Catalyst | Amount | Time (hrs) | % Yield |
|---|---|---|---|
| NPDBAPB[c] | 2% | 1 | 60 |

TABLE III-continued

| Catalyst | Amount | Time (hrs) | % Yield |
|---|---|---|---|
| NPDBAPB | 2% | 2 | 85 |
| NPDBAPB | 3% | 1 | 86 |
| NPDBAPB | 3% | 2 | 96 |
| NPDBAPB | 4% | 1 | 99 |
| NPDBAPB | 5% | 1 | 99 |
| NPDBAPB | 10% | .5 | 98 |
| NPDMAPB[d] | 5% | 1 | 85 |
| NPDHAPB[e] | 1.8% | 1 | 65 |
| NPDHAPB | 2.5% | 1 | 84 |
| NPDHAPB | 3% | 1 | 95 |
| NPDHAPP | 4% | 1 | 98 |
| NPDBAPNO2[f] | 4% | 1 | 90 |
| NPDBAPOMs[g] | 4% | 1 | 89 |
| NPDBAPB[h] | 4% | 2 | 75 |
| NPTBPB[i] | 5% | 1 | 47 |
| NPHOPB[j] | 5% | 1 | 63 |
| NPDBAPCl[k] | 4% | 1 | 98 |

[a]All reactions were run in refluxing toluene at 90% solids using 1.0 mmole BPA disodium salt. and 2.00 mmole 4-Nitro-N—methylphthalimide. Yields were measured by HPLC analysis at 285 nm using 9-fluorenone as internal standard.
[b]Mole percent catalyst with respect to BPA disodium salt.
[c]N—neopentyl-4-N,N—dibutylaminopyridinium bromide:
[d]N,N—dimethylamino
[e]N,N—dihexylamino
[f]Nitrite salt
[g]Methanesulfonate salt
[h]6% BPA added
[i]N—neopentyl-4-tert-butylpyridinium bromide
[j]N—neopentyl-4-n-hexoxy-pyridinium bromide:
[k]Chloride salt The above results further establish the superiority of the diorganopyridinium salts as phase transfer catalysts for the production aromatic etherimides or aromatic bis(ether phthalimides) as compared to tetraalkylamino or phosphonium halides as phase transfer catalysts.

Although the above examples are directed to only a few of the very many variables which can be used in the practice of the method of the present invention, or to the diorganopyridinium phase transfer catalysts, it should be understood that the present invention is directed to a much broader variety of diorganoaminopyridinium salts and to the use of phase transfer catalysts in the production of aromatic ethers, such as aromatic bisether phthalimides.

What we claim as new and desire to secure by Letters Patent of the United States is:

1. In the method for making an aromatic ether comprising the reaction between a nuclear activated aromatic compound substituted with a leaving group selected from a nitro or halo radical and an alkali metal phenoxide in the presence of a phase transfer catalyst, the improvement which comprises utilizing as the phase transfer catalyst a diorganoaminopyridinium salt of the formula,

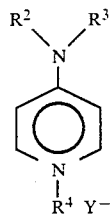

where $R^2$ and $R^3$ are monovalent or divalent organo radicals selected from $C_{(1-13)}$ hydrocarbon radicals and $C_{(1-13)}$ substituted hydrocarbon radicals and $C_{(1-8)}$ divalent alkylene radicals which can be part of a cyclic structure forming a $C_{(4-12)}$ ring, $R^4$ is selected from $C_{(4-18)}$ linear or branched alkyl radicals and Y is a counter ion.

2. A method in accordance with claim 1, where the nuclear activated aromatic compound is a nuclear substituted phthalimide.

3. A method in accordance with claim 1, where the alkali metal phenoxide is the disodium salt of bisphenol-A.

4. A method in accordance with claim 1, where the diorganoaminopyridinium salt is N-neopentyl-4-(4-methylpiperidinyl)pyridinium chloride.

5. A method in accordance with claim 1, where the diorganoaminopyridinium salt is N-neopentyl-4-dibutylaminopyridine.

6. A method in accordance with claim 1, where the diorganoaminopyridinium salt is N-neopentyl-4-dihexylaminopyridine.

7. A method for making aromatic etherimides of the formula

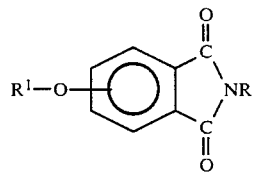

which comprises, (A) heating a substituted phthalimide of the formula

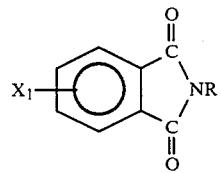

and an alkali metal phenoxide salt of the formula $(R^1\text{—OM})_a$ in the presence of organic solvent and an effective amount of a phase transfer catalyst of the formula

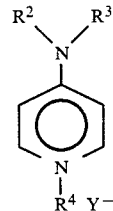

(B) agitating the resulting mixture with a precipitating or extractive organic solvent for the resulting aromatic etherimide, or allowing the mixture to cool and (C) recovering the aromatic ether imide from the mixture of (B)

where R is a monovalent radical selected from hydrogen, a $C_{(1-8)}$ alkyl radical and $C_{(6-13)}$ aryl radical, $R^1$ is a $C_{(6-30)}$ aromatic organic radical, where $R^2$ and $R^3$ are monovalent or divalent organo radicals selected from $C_{(1-13)}$ hydrocarbon radicals and $C_{(1-13)}$ substituted hydrocarbon radicals and $C_{(1-8)}$ divalent alkylene radicals which can be part of a cyclic structure forming a $C_{(4-12)}$ ring, $R^4$ is selected from $C_{(4-18)}$ linear or branched alkyl radicals and Y is a counter ion, M is an alkali metal ion, $X_1$ is a radical selected from nitro and halo, and a is an integer equal to 1 to 2, and when a is 1, $R^1$ is monovalent and when a is 2, $R^1$ is divalent.

8. A method in accordance with claim 7, utilizing an alkali metal monophenoxide salt.

9. A method in accordance with claim 7, utilizing an alkali metal diphenoxide salt.

10. A method in accordance with claim 7, where the alkali metal salt is the anhydrous disodium salt of bisphenol-A.

11. A method in accordance with claim 7, where the alkali metal phenoxide salt is made by azeotroping water from a mixture of toluene and the hydrated form of the alkali metal phenoxide salt.

12. A method in accordance with claim 7, where the alkali metal phenoxide salt is formed in situ from an aqueous mixture of the alkali metal hydroxide and the corresponding phenol.

13. A method in accordance with claim 7, where the alkali metal phenoxide salt is made from a mixture of an alkali metal alkoxide and the corresponding monohydric or dihydric phenol.

14. A method in accordance with claim 7, where the substituted phthalimide is 3-nitro-N-methylphthalimide.

15. A method in accordance with claim 7, where the substituted phthalimide is 4-fluoro-N-methyl or N-phenyl phthalimide.

16. A method in accordance with claim 7, where the substituted phthalimide is 4-nitro-N-methyl or N-phenyl phthalimide.

17. A method in accordance with claim 7, where the alkali metal phenoxide is an alkali bisphenoxide of a dihydric sulfone.

18. A method in accordance with claim 7, where the alkali metal phenoxide is an alkali bisphenoxide of a dihydric sulfide.

* * * * *